(12) United States Patent
Karolchyk

(10) Patent No.: US 11,857,589 B2
(45) Date of Patent: *Jan. 2, 2024

(54) WATER-SOLUBLE, POWDERED CANNABINOID AND/OR TERPENE EXTRACT

(71) Applicant: MEDPHARM HOLDINGS, LLC, Denver, CO (US)

(72) Inventor: Scott Karolchyk, Denver, CO (US)

(73) Assignee: MEDPHARM HOLDINGS, LLC, Denver, CO (US)

( * ) Notice: Subject to any disclaimer, the term of this patent is extended or adjusted under 35 U.S.C. 154(b) by 492 days.

This patent is subject to a terminal disclaimer.

(21) Appl. No.: 17/204,397

(22) Filed: Mar. 17, 2021

(65) Prior Publication Data

US 2021/0196775 A1 Jul. 1, 2021

Related U.S. Application Data

(63) Continuation-in-part of application No. 16/576,162, filed on Sep. 19, 2019, now Pat. No. 10,980,743.

(60) Provisional application No. 62/733,294, filed on Sep. 19, 2018.

(51) Int. Cl.
| | | |
|---|---|---|
| *A61K 36/185* | (2006.01) |
| *A61K 9/107* | (2006.01) |
| *A61K 47/44* | (2017.01) |
| *A61K 47/40* | (2006.01) |
| *A61K 47/02* | (2006.01) |
| *A61K 47/36* | (2006.01) |

(52) U.S. Cl.
CPC ............ *A61K 36/185* (2013.01); *A61K 9/107* (2013.01); *A61K 47/02* (2013.01); *A61K 47/36* (2013.01); *A61K 47/40* (2013.01); *A61K 47/44* (2013.01)

(58) Field of Classification Search
None
See application file for complete search history.

(56) References Cited

FOREIGN PATENT DOCUMENTS

WO WO 2020222029 A1 * 11/2020

* cited by examiner

*Primary Examiner* — Michael V Meller
(74) *Attorney, Agent, or Firm* — NYEMASTER GOODE, P.C.

(57) ABSTRACT

The invention relates to the preparation of a water soluble, powdered pharmaceutically active cannabinoid and/or terpene extract from plant materials or of synthetic origin. The extract is first treated with a solvent to solubilize the cannabinoids, then combined with an emulsifier. The solubilized mixture is then dried to evaporate the solvent, leaving the water-soluble cannabinoid extract powder. The resulting powder remaining stable at room temperature for at least one year and can be compounded into various pharmaceutical powdered formulations.

1 Claim, No Drawings

WATER-SOLUBLE, POWDERED CANNABINOID AND/OR TERPENE EXTRACT

CROSS-REFERENCE TO RELATED APPLICATIONS

This application claims the benefit of priority to U.S. Non-Provisional patent application Ser. No. 16/576,162, filed Sep. 19, 2019, entitled "WATER SOLUBLE, POWDERED CANNABINOID AND/OR TERPENE EXTRACT," which claims the benefit of priority to U.S. Provisional Patent Application No. 62/733,294, filed Sep. 19, 2018, entitled "WATER SOLUBLE, POWDERED CANNABINOID AND/OR TERPENE EXTRACT, the entire disclosures of which are hereby incorporated by reference in their entireties.

FIELD OF THE INVENTION

This invention relates to the preparation of a water soluble, powdered cannabinoid and/or terpene extract (THC, THC/CBD, CBD and terpene) from pharmaceutically active components from plant materials and synthetically derived, a powder where the bulk density can easily be changed based on the final dosage form desired.

BACKGROUND OF THE INVENTION

Cannabinoids are diverse chemical compounds acting on cannabinoid receptors CB1 and CB2. Cannabis has been used for medicinal purposes for thousands of years. Its active compounds produce pharmacological effects throughout the body, especially in the central nervous system and the immune system. There presently exists the need to provide more effective, bioavailable and safer cannabis dosage forms for various medical uses, including treatment of pain, nausea, spasticity in multiple sclerosis, side effects of chemotherapy, and various other medical conditions.

The disadvantages of currently available oral formulations of cannabis include slow and insufficient absorption and delayed onset of action and low systemic availability, largely due to the highly lipophilic nature of cannabinoids. Formulation of cannabinoids as aerosols, sprays, eye drops, etc. requires aqueous solutions of these highly lipophilic active compounds. Current attempts at solubilizing cannabinoids have included the use of various types of sugar molecules such as cyclodextrins (CDs). CDs, however, are very expensive and difficult to work with. For these and other reasons, there is a need for the present invention.

SUMMARY OF THE INVENTION

The invention provides a unique, water soluble, powdered cannabinoid and/or terpene extract (THC, THC/CBD, CBD and terpene) and a method of manufacturing and using the same. The invention allows extracted cannabinoid oil to be used in formulations containing dry powders such as tablets, capsules, dry powder inhalers, edibles, beverages and powdered mixes. The powder's bulk density can easily be modified based on the final dosage form in development and to match formulation granulation. Potency of the powder is modifiable as well.

The method includes first combining a cannabinoid extract with a solvent or solvent mixture that is capable of solubilizing the cannabinoid. Once dissolved, the mixture is combined with one or more water soluble emulsifying sugar substrates which absorb the oil from the extract and make the extract components water soluble. The solubilized mixture is then dried to evaporate the solvent, leaving the water-soluble cannabinoid extract powder. The resulting powder remaining stable at room temperature for at least one year and can be compounded into various pharmaceutical powdered formulations.

Other features and advantages of the invention will be apparent from and are encompassed by the following detailed description and claims.

DETAILED DESCRIPTION OF THE PREFERRED EMBODIMENT

The present invention relates to a unique method of solubilizing cannabinoid extract/distillate for use in formulating pharmaceutical compositions containing dry powders, including tablets, capsules, dry powder inhalers, edibles, beverages and powdered mixes. The inventor has surprisingly discovered that extracts from cannabinoids can be effectively and inexpensively solubilized using a solvent and a combination of emulsifiers. The resulting composition is a water-soluble powder that may in turn be used in pharmaceuticals.

The cannabis extracts of the invention are any that can be derived or extracted from cannabis plants, hemp or synthetically derived. Cannabis plants produce a unique family of terpeno-phenolic compounds called cannabinoids, which produce the "high" one experiences from consuming marijuana. There are 483 identifiable chemical constituents known to exist in the cannabis plant, and at least 185 different cannabinoids have been isolated from the plant. The two cannabinoids usually produced in greatest abundance are cannabidiol (CBD) and/or (−)-trans-$\Delta^9$-tetrahydrocannabinol (THC), but only THC is psychoactive. Thus, as used here, the term "cannabis" is intended to include not only cannabis, but hemp, synthetic cannabinoids, and terpenes.

Cannabis plants are categorized by their chemical phenotype or "chemotype," based on the overall amount of THC produced, and on the ratio of THC to CBD. Although overall cannabinoid production is influenced by environmental factors, the THC/CBD ratio is genetically determined and remains fixed throughout the life of a plant. Non-drug plants produce relatively low levels of THC and high levels of CBD, while drug plants produce high levels of THC and low levels of CBD. Besides CBD and THC, other cannabinoids include, but are not limited to, cannabichromene (CBC), cannabigerol (CBG) cannabinidiol (CBND), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), and all acidic forms, precursors, and derivatives thereof. Cannabinoids are derived from their respective 2-carboxylic acids (2-COOH) by decarboxylation (catalyzed by heat, light, or alkaline conditions). As a general rule, the carboxylic acid form of the cannabinoid have the function of a biosynthetic precursor.

As noted, the present invention relates to the solubilization of use of any cannabis plant extract in any form. In addition to cannabinoids, cannabis plants produce terpenes, a diverse group of organic hydrocarbons that are the building blocks of the cannabinoids. Over 100 different terpenes have been identified in the cannabis plant, and every strain tends toward a unique terpene type and composition. The terpenes act synergistically with the cannabinoids to provide a therapeutic effect. The terpenes in the extract include, but are not limited to, myrcene, alpha-bisabolol, caryophyllene, limonene, eucalyptol, nerolidol, terpineol, camphene, valencene, geraniol, humulene, delta-3-carene, borneol, alpha-pinene and beta-pinene, and linalool. In various aspects the invention provides cannabis extracts with predefined ratios of cannabinoids. Standard conditions for cannabinoid assays, and methods of calculating cannabinoid content (as %) are well known in the art.

The cannabinoid extract starting materials are typically mixtures of at least 90% total cannabinoids which include terpenes and/or flavonoids. Preferably the extracts contain a mixture of at least four cannabinoid such as tetrahydrocannabinolic acid (THCa), cannabidiolic acid (CBDa), cannabinolic acid (CBNa) cannabichromenic acid (CBCa), tetrahydrocannabinol (THC), cannabinol (CBN), cannabidiol (CBD) and cannabichromene (CBC). The terpene and/or flavonoids in the extract include, but are not limited to, myrcene, alpha-bisabolol, caryophyllene, limonene, eucalyptol, nerolidol, terpineol, camphene, valencene, geraniol, humulene, delta-3-carene, borneol, alpha-pinene and beta-pinene, and linalool.

Therefore, in a further aspect the invention provides a method of making a water soluble powdered extract composition comprising, as an active agent, a substance which is an extract from at least one cannabis plant variety.

Separate extracts may be prepared from single cannabis plant varieties having differing cannabinoid content (e.g. high THC and high CBD plants) and then mixed or blended together prior to formulation to produce the final pharmaceutical composition. This approach is preferred if, for example, it is desired to achieve a defined ratio by weight of individual cannabinoids in the final formulation. Alternatively, plant material from one or more cannabis plant varieties of defined cannabinoid content may be mixed together prior to extraction of a single botanical drug substance having the desired cannabinoid content, which may then be formulated into a final pharmaceutical composition.

A preferred formulation includes a cannabinoid mixture where THC is greater than or equal to 90%; a CBD is less than 1%; CBN is less than 3%; and CBC is less than 1%. In some aspects the formulation further includes d-limonene, linalool, 1,8-cineole (eucalyptol), alpha-pinene, terpineol-4-ol, p-cymene, borneol, delta-3-carene, beta-sitosterol, cannflavin A, apigenin, and quercetin.

Another preferred formulation includes a cannabinoid mixture where the THC is less than or equal to 30%; CBD is greater than or equal to 60%; CBN is less than 1%; and CBC is less than 1%. In some aspects the formulation further includes d-limonene, linalool, 1,8-cineole (eucalyptol), alpha-pinene, terpineol-4-ol, p-cymene, borneol, delta-3-carene, beta-sitosterol, cannflavin A, apigenin, and quercetin.

In yet another preferred embodiment the formulation includes a cannabinoid mixture where the THC is greater than or equal to 45%; CBD is greater than or equal to 45%; CBN is less than 1%; and CBC is less than 1%. In some aspects the formulation further includes beta-myrcene, beta-caryophyllene, pulegone, alpha-terpineol, beta-sitosterol, cannflavin A, apigenin, and quercetin.

In accordance with the methods of the invention, the constituents of the powdered extract may all be combined at once, or combined in stages. The following materials may be used to manufacture the powdered extract of the claimed invention:

from about 0.1-85% by weight cannabinoid extract, terpene extract, or combinations thereof, with about 10-50% by weight being preferred, and about 20-30% by weight being most preferred;

from about 0.1-75% by weight solvent, with about 20-60% by weight being preferred, and about 20-40% by weight being most preferred;

from about 0.1-80% by weight carbohydrate substrate, with about 20-60% by weight being preferred, and about 30-50% by weight being most preferred.

In one embodiment of the invention, cannabinoid extract is first combined with an emulsifier(s) and a pharmaceutically acceptable solvent to form a dissolved extract. The solvent is one that is capable of dissolving the extract but one that does not dissolve the substrate emulsifier used in the second step. The solvent also needs to be one that can be evaporated or otherwise incorporated into from the composition to form the resulting powder. Suitable class 1-3 solvents for this purpose include, but are not limited to, n-hexane, ethyl acetate, diethyl ether, 2-propanol, acetone, ethanol, ethanol/water, butane, propane, benzyl alcohol, 1,3-butylene glycol, citric acid esters of mono- and di-glycerols, glycerin, glyceryl triacetate, glyceryl tributyrate, isopropyl alcohol, monoglyceride citrate, propylene glycol, triethyl citrate, diethylene glycol and propylene glycol mono- and de-esters. In one embodiment of the invention, the solvent is 95% ethanol.

The solvent is combined with the extract in an amount sufficient to dissolve the components of the extract. In one embodiment, the solvent is combined with equal parts extract. The solvent/extract mixture is preferably heated to a range of about 50-85° C. with about 50-60° C. being preferred and about 55° C. being most preferred. The mixture may optionally be stirred/agitated to more thoroughly combine the ingredients.

The dissolved extract is next combined with an emulsifier and/or emulsifying system to form a water-soluble powder. The cannabinoids absorb onto and are coated by the substrate emulsifier. Thus, the emulsifier is used to absorb the oil and make the extract water soluble.

The emulsifier is preferably a sugar or carbohydrate substrate that may include, but is not limited to, starch, maltodextrins, glucose syrup, crystalline glucose (dextrose, sucrose, fructose), poloxamers including 188 and 407, caramel, sorbitol, maltitol, mannitol, isomalt, beta/hydroxypropyl cyclodextrins, lecithin, soy-derived glycerol phosphatides, acacia, gum arabic, xanthan gum, carrageenan, polyglycols, poloxamers, hydroxystearate polyoxyl 15 (Kolliphor HS15), locust bean gum, tapioca, carboxymethylcellulose, sodium tripolyphosphate (STPP), and combinations of the same. In one embodiment, the emulsifying system includes an oil soluble emulsifier combined with a water soluble emulsifier. In another embodiment, the emulsifying system is a combination of maltodextrin and gum arabic (acacia). In one embodiment, the emulsifying system includes STPP in a concentration of about 0.1-5% by weight.

In one embodiment of the invention, the dissolved and/or emulsified extract may also include one or more other components or methods to improve the solubility and/or dissolution rate of the extract. For example, the cannabis and/or other active ingredients of the invention may be complexed with cyclodextrins. Cyclodextrins are molecular donut-shaped structures consisting of several glucose molecules. Depending on the denotation (alpha-, beta-, or gamma cyclodextrins), 6 to 8 glucopyranose units are cyclically joined to make a "truncated cone". The interior diameter of the structure measures between 0.6 nm to 0.8 nm. Due to the orientation of the carbons of the sugars, the polarity of the cavity is comparable to the polarity of ethanol, which provides a local favorable environment for lipophilic drugs. However, solubility enhancement with cyclodextrins is restricted by their cavity size: the alpha form does not provide sufficient space for many drug molecules, and the larger gamma form is comparably expensive. The complexation of a drug with cyclodextrin furthermore leads to an enhanced dissolution rate.

Mesoporous silica refers to any number of a variety of materials synthesized to produce a $SiO_2$ mesoporous structure. Mesoporous silica can be ordered or non-ordered. It has been widely reported that mesoporous silica can act as a solubility enhancer by adsorbing and stabilizing active pharmaceutical ingredients (APIs) in the amorphous form within the porous network.

There are various methods of loading crystalline API onto mesoporous silica, which can be grouped into three broad categories: solvent-based, mechanical activation, and vapor-mediated. API is dissolved in organic solvent (thus removing any crystal lattice) and added to mesoporous silica. Adsorption of API onto the silica is then initiated through mechanical agitation or sonication of the slurry. Finally, solvent is removed, which can be achieved using a number of methods including vacuum drying, spray drying, lyophilization or rotary evaporation. The cannabis or other active ingredients of the invention may be loaded onto the silica through conventional methods well known to persons skilled in the art.

Mesoporous silica has particular advantages in pre-clinical development due to the low capital investment requirements and relatively accessible loading method. The loading of mesoporous silica can be achieved using simple laboratory equipment and scaled to commercial batches using regular manufacturing equipment.

Mesoporous silica materials (MSMs) are characterized by very large surface areas, uniform pore size, significant biocompatibility and easy surface functionalization. Generally, MSMs are prepared by hydrolysis and condensation of silica precursors such as tetraethoxysilane (TEOS) around the micelle templates (generated by supramolecular self-assemblies of surfactant molecules) followed by template removal by calcination or solvent extraction. There are two common mechanisms, i.e., cooperative self-assembly of micelle and silica source and liquid-crystal templating to describe the synthesis of MSMs. MSMs can be prepared with different sizes from nanoscale to microscale range, with large surface area (from 700 to 1000 $m^2/g$) and pore volume (from 0.6 to 1 $cm^2/g$). Also, depending on the reaction condition, diverse morphologies (e.g., spherical, rod, ellipsoid, and platelet) can also be made each suitable for a specific biological application. While typical pore diameters of MSMs are ~2-5 nm, it is also possible to synthesize pore diameter up to 30 nm, thereby allowing accommodating not only small molecules but also larger chemicals such as proteins within the mesopores. Furthermore, owing to surface silanol groups, the surface properties of MSMs can range from hydrophobic to hydrophilic, thus providing the possibility of a proper drug loading parameters as well as drug release profile for different drug substances.

The substrate is preferably selected according to the bulk density necessary for the pharmaceutical product in which the final powder product is incorporated, as well as to match formulation granulation. For instance, if the powder will be used to formulate a tablet, the substrate should have a higher bulk density, while a nasal inhalation pharmaceutical will have a lower bulk density. The types of pharmaceuticals and their desired bulk densities, and appropriate substrates to achieve such bulk densities are as follows (ratios of each can change):

compressed tablet, bulk density of 0.4-1.5 $g/cm^3$, appropriate substrates: spray dried lactose or direct compression lactose/acacia/STPP/poloxamer 188;

immediate-release tablet, bulk density of 0.2-1.5 $g/cm^3$, appropriate substrates: sieved lactose/acacia/STPP/poloxamer;

powder, bulk density of 0.1-1.0 $g/cm^3$, appropriate substrates: maltodextrin or milled lactose/acacia/STPP/poloxamer;

dry-granulations, bulk density of 0.4-1.5 $g/cm^3$, appropriate substrates: milled lactose/acacia/STPP/poloxamer;

oral inhalation powder, bulk density of 0.1-0.5 $g/cm^3$, appropriate substrates: fine milled and sieved lactose/acacia/STPP/poloxamer/CD The process can be applied to a range of core materials in numerous particles sizes and shapes and densities. No matter the shape, crystalline, spherical, irregular, amorphous, the process is capable of creating unique formulations to achieve the desired properties. Understanding the flow related properties, particle size and density is critical in the processing of these powders for their intended formulations. This invention eliminates most trial and error.

If an emulsifying system is used, the system includes about 1:20-20:1 water soluble emulsifier to oil soluble emulsifier. In one embodiment, the system includes about 5% by weight oil soluble emulsifier to about 95% by weight water soluble emulsifier. A higher concentration of substrate, with or without emulsifier, will result in higher solubility of the final powder composition. The carbohydrate substrates themselves act as emulsifiers/colloids allowing the water insoluble colloids, cannabinoids or other drugs to become solubilized. The ratios of substrate alone or in combination with other emulsifiers allow for easy wetting and enhanced solubility, which is further enhanced as dilution continues.

In one embodiment, the dissolved extract is sprayed onto the emulsifier while the emulsifier is under agitation and vacuum. In a preferred embodiment, a Ross vertical cone screw blender is utilized whereby the powdered solids are combined under vacuum then immediately subjected to high sheer mixing at a point in the blender where flow if most turbulent. In another embodiment, the dissolved extract is dripped into the emulsifier while mixing. If more than one emulsifier is used in this step it is preferred to mix the emulsifiers prior to combining with the dissolved extract.

In one embodiment of the invention, the extract is ultrasonically homogenized or microfluidized to form microemulsions and nanoemulsions. When added to liquids, the resulting homogenized extracts are tasteless and translucent, as compared to most emulsifiers used in microemulsions which have a strong, bitter taste. In one embodiment, the globule sizes are less than about 100 nm, with an average globule size of about 50 nm. The key to the invention in this respect is the combination, ratio, and concentration of the carbohydrate components.

The solvent/extract mixture is next dried to form a micronized powder by preferably heating the mixture for several hours to a range of about 50-85° C. with about 50-60° C. being preferred and about 55° C. being most preferred. The mixture may optionally be stirred/agitated during this step to more thoroughly combine the ingredients. In one embodiment, the mixture is agitated under vacuum. The solvent/extract mixture may also be dried using conventional methods including, but not limited to, air drying, spray drying, freeze drying, etc. The mixture is dried and/or placed under vacuum for a time period sufficient to provide a flowable powder free of aggregates, with a moisture content generally ranging from about 2-8% by weight, with about 4% moisture by weight being preferred. The powdered product may be further processed into consumer and pharmaceutical formulations and/or used for testing. In another embodiment, small batches of product may be prepared by hand on a benchtop.

The resulting micronized powder has a particle size of no more than 5000 nm, with a resulting particles size of about 20-1000 nm to as small as about 20-50 nm depending upon the amount and extent of processing. Unlike other known preparation methods, the resulting product does not require encapsulation and/or microencapsulation. The product and its method of processing are further distinguished from prior methods in that the materials do not require sterilization during any of the processing steps.

The preparation of the compositions of the invention may be easily scaled up with the use of equipment that is known in the art including, but not limited to, Wurster fluidizer, vertical blender with vacuum and spray dryer, and/or hand spraying/mixing. The compositions of the invention may be inexpensively manufactured on a commercial scale. A wet solution is sprayed into the fluid bed coater to agglomerate the primary powder together and create larger granules by suspending the particles inside the chamber through high velocity air. This material is then dried upon completion of the spraying by hot air to the unit. The particles exit the chamber in different shapes, sizes and densities based on the movement of the material in the chamber and through particle interaction. The powder is flowable and stable against oxidation and moisture.

The water soluble powdered extract may be formulated with any convenient pharmaceutically acceptable diluents, carriers or excipients to produce a pharmaceutical composition. The choice of diluents, carriers or excipients will depend on the desired dosage form, which may in turn be dependent on the intended route of administration to a patient. Oral dosage forms include, but are not limited to, tablets, capsules, suspensions, granules, and solutions. The pharmaceutical preparations of the present invention are manufactured in a manner which is itself well known in the art. For example the pharmaceutical preparations may be made by means of conventional mixing, granulating, dissolving, lyophilizing processes and vibrational atomization. The processes to be used will depend ultimately on the physical properties of the active ingredient used.

Suitable excipients are, in particular, fillers such as sugars for example, lactose or sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices. For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combinations of compound doses.

Other pharmaceutical preparations which can be used orally include capsules made of gelatin, as well as soft, sealed capsules made of gelatin and a plasticizer such as glycerol or sorbitol. The capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids; such as fatty oils, liquid paraffin, or liquid polyethylene glycols. In addition stabilizers may be added.

The pharmaceutical preparations of the present invention are manufactured in a manner which is itself well known in the art. For example the pharmaceutical preparations may be made by means of conventional mixing, granulating, dissolving, lyophilizing processes. Such dosage forms may be prepared in accordance with standard principles of pharmaceutical formulation, known to those skilled in the art. The extract may be formulated for oral use (e.g. capsules) in dosage forms that provide, for example, less than 5 mg, 5 mg, 10 mg, 20 mg, 100 mg, or more than 100 mg of total cannabinoids per dose.

The following examples are offered to illustrate but not limit the invention. Thus, it is presented with the understanding that various formulation modifications as well as method of delivery modifications may be made and still are within the spirit of the invention.

Example 1

A pharmaceutical composition was prepared as described below. The following products were used in the amounts and concentrations specified:
1. About 20 g cannabinoid distillate
2. About 35 g Ethanol 95%
3. About 40 g maltodextrin/gum acacia mixture The cannabinoid distillate was weighed in a glass beaker. Ethanol 95% was added to the same beaker. The contents of the beaker were allowed to dissolve on a hot plate set to 55° C.

The above solution was combined with the maltodextrin/gum acacia in a planar mixer and was gently mixed until well incorporated.

The above mixture was passed through a granulation screen into a second bowl. This bowl was placed into a vacuum oven at 55° C. for 12 hours. The powder was stirred at least one during this time frame.

The formulation above was tested for potency and stability after 1 year of storage. After this period, no loss of potency was observed (as measured by HPLC), the formulation was visibly stable at room temperature and readily fluid when shaken.

Example 2

A pharmaceutical composition was prepared as described below. The following products were used in the amounts and concentrations specified:
1. The cannabinoid distillate (or terpenes or isolate or combinations thereof) is weighed into a glass beaker.

The beaker was tared and then ethanol 95% was weighed into the same beaker. The contents of the beaker were allowed to completely dissolve on a hot plate set to 55° C.

2. Maltodextrin/gum acacia powder was weighed into a glass mixing vessel with paddle attachment.
3. The product of step 1 was slowly dripped into the maltodextrin/acacia powder while mixing with vertical blender using gentle shear.
4. After the distillate/solvent has been added the powder is mixed for an additional 5 minutes.
5. The wetted powder is passed through a 3.35 mm granulation screen and allowed to dry in a vacuum oven set to 55° C. for at least 12 hours.
6. The powder was gently mixed at 2 hours and 6 hours.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplish at least all of the intended objectives.

What is claimed is:

1. A water-soluble, micronized, emulsified, powdered cannabis extract, said cannabis extract complexed with a cyclodextrin; said powdered cannabis extract being emulsified with a combination of maltodextrin and acacia; said powdered cannabis extract having been loaded onto a mesopores silica.

* * * * *